US012788281B2

(12) United States Patent
Gu et al.

(10) Patent No.: US 12,788,281 B2
(45) Date of Patent: Nov. 10, 2026

(54) COLLOIDAL CRYSTAL MICRONEEDLE PATCH FOR GLUCOSE MONITORING

(71) Applicant: THE REGENTS OF THE UNIVERSITY OF CALIFORNIA, Oakland, CA (US)

(72) Inventors: Zhen Gu, Los Angeles, CA (US); Yi Zeng, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 676 days.

(21) Appl. No.: 18/261,591

(22) PCT Filed: Jan. 19, 2022

(86) PCT No.: PCT/US2022/012973
§ 371 (c)(1),
(2) Date: Jul. 14, 2023

(87) PCT Pub. No.: WO2022/159486
PCT Pub. Date: Jul. 28, 2022

(65) Prior Publication Data

US 2024/0108253 A1 Apr. 4, 2024

Related U.S. Application Data

(60) Provisional application No. 63/140,206, filed on Jan. 21, 2021.

(51) Int. Cl.
*C08J 3/075* (2006.01)
*A61B 5/00* (2006.01)
(Continued)

(52) U.S. Cl.
CPC .......... *A61B 5/14532* (2013.01); *A61B 5/685* (2013.01); *C08J 3/075* (2013.01);
(Continued)

(58) Field of Classification Search
None
See application file for complete search history.

(56) References Cited

U.S. PATENT DOCUMENTS 8,452,356 B2 * 5/2013 Vestel .................. A61B 5/6849
600/310
10,980,992 B2 4/2021 Gu et al.
(Continued)

FOREIGN PATENT DOCUMENTS

WO WO 2017/143153 A1 8/2017
WO WO 2017/151727 A1 9/2017
(Continued)

OTHER PUBLICATIONS

Colloidal crystal microneedle patch for glucose monitoring (Year: 2020).*

(Continued)

*Primary Examiner* — Peter A Salamon
(74) *Attorney, Agent, or Firm* — VISTA IP LAW GROUP LLP

(57) ABSTRACT

A minimally invasive glucose-responsive colloidal crystal microneedle (GCC-MN) patch is disclosed for naked-eye glucose monitoring. The (GCC-MN) patch is designed with a resin or polymeric core to mechanically support a shell of glucose-responsive colloidal crystal material for glucose sensing and reporting of glucose concentrations or concentration changes. The GCC-MN patch could translate the glucose concentrations into naked-eye distinguishable color changes within about 5 min, and such glucose responsiveness is reversible. Demonstrated in a type 1 diabetic mouse model, the interstitial fluid extraction, glucose sensing, and resulting glucose-relevant color display procedures are simultaneously achieved with this GCC-MN patch.

18 Claims, 11 Drawing Sheets

(51) Int. Cl.
*A61B 5/145* (2006.01)
*C08J 3/28* (2006.01)
*C08K 3/36* (2006.01)

(52) U.S. Cl.
CPC .................. *C08J 3/28* (2013.01); *C08K 3/36* (2013.01); *C08J 2343/00* (2013.01)

(56) References Cited

U.S. PATENT DOCUMENTS

| | | | | |
|---|---|---|---|---|
| 11,351,230 | B2 | 6/2022 | Gu et al. | |
| 2002/0006355 | A1* | 1/2002 | Whitson ............ | A61B 5/14532 422/550 |
| 2010/0121163 | A1* | 5/2010 | Vestel ................ | A61B 5/14532 600/316 |
| 2019/0015515 | A1 | 1/2019 | Gu et al. | |
| 2019/0083703 | A1 | 3/2019 | Gu et al. | |
| 2019/0151639 | A1* | 5/2019 | Mou ...................... | G16H 20/17 |
| 2019/0160272 | A1 | 5/2019 | Gu et al. | |
| 2019/0351206 | A1 | 11/2019 | Gu et al. | |
| 2020/0330562 | A1 | 10/2020 | Gu et al. | |
| 2020/0360269 | A1 | 11/2020 | Gu et al. | |
| 2021/0236786 | A1 | 8/2021 | Gu et al. | |
| 2021/0244658 | A1 | 8/2021 | Gu et al. | |
| 2021/0260198 | A1 | 8/2021 | Gu et al. | |
| 2021/0380965 | A1 | 12/2021 | Wei et al. | |
| 2022/0160841 | A1 | 5/2022 | Gu et al. | |

FOREIGN PATENT DOCUMENTS

| | | | | |
|---|---|---|---|---|
| WO | WO 2018/085809 | A1 | 5/2018 | |
| WO | WO 2018/106696 | A1 | 6/2018 | |
| WO | WO-2019104006 | A1 * | 5/2019 | ............. A61K 47/58 |
| WO | WO 2021/225826 | A1 | 11/2021 | |
| WO | WO 2021/252673 | A1 | 12/2021 | |
| WO | WO 2022/119868 | A2 | 6/2022 | |
| WO | WO 2022/119868 | A3 | 6/2022 | |
| WO | WO 2022/178164 | A1 | 8/2022 | |
| WO | WO 2023/056171 | A1 | 4/2023 | |

OTHER PUBLICATIONS

PCT International Search Report for PCT/US2022/012973, Applicant: The Regents of the University of California, Form PCT/IB/326 and 373, dated Aug. 3, 2023 (6 pages).

Akira Matsumoto et al., A Synthetic Approach Toward a Self-Regulated Insulin Delivery System, Angew. Chem. Int. Ed. 2012, 51, 2124-2128.

PCT International Search Report for PCT/US2022/012973, Applicant: The Regents of the University of California, Form PCT/ISA/210 and 220, dated Apr. 7, 2022 (3 pages).

PCT Written Opinion of the International Search Authority for PCT/US2022/012973, Applicant: The Regents of the University of California, Form PCT/ISA/237, dated Apr. 7, 2022 (4 pages).

Yi Zheng et al., Colloidal crystal microneedle patch for glucose monitoring, Nano Today, 35 (2020) 100984.

Vladimir L. Alexeev et al., Photonic Crystal Glucose-Sensing Material for Noninvasive Monitoring of Glucose in Tear Fluid, Clinical Chemistry 50:12, 2353-2360 (2004).

Sanford A. Asher et al., Photonic Crystal Carbohydrate Sensors: Low Ionic Strength Sugar Sensing, J. Am. Chem. Soc., (2003), 125, 3322-3329.

Mohamed Elsherif et al., Wearable Contact Lens Biosensors for Continuous Glucose Monitoring Using Smartphones, ACS Nano 2018, 12, 5452-5462.

John Holtz et al., Polymerized Colloidal Crystal Hydrogel Films as Intelligent Chemical Sensing Materials, Nature, vol. 389, 829-832, (Oct. 23, 1997).

Xiaodi Hong et al., A Novel Opal Closest-Packing Photonic Crystal for Naked-Eye Glucose Detection, Small, (2014), 10, No. 7, 1308-1313.

Kwang Bok Kim et al., Continuous glucose monitoring using a microneedle array sensor coupled with a wireless signal transmitter, Sensors & Actuators: B. Chemical 281 (2019) 14-21.

Hyunjae Lee et al., A graphene-based electrochemical device with thermoresponsive microneedles for diabetes monitoring and therapy, Nature Nanotechnology, Published Online, (Mar. 21, 2016), DOI:10.1038/NNANO.2016.38.

KangJu Lee et al., Non-transdermal microneedles for advanced drug delivery, Advanced Drug Delivery Reviews, 165-166 (2020) 41-59.

Yukikazu Takeoka et al., Simple and Precise Preparation of a Porous Gel for a Colorimetric Glucose Sensor by a Templating Technique, Angew. Chem., (2003), 115, 4329-4332.

Dean Nicholas et al., Rapid paper based colorimetric detection of glucose using a hollow microneedle device, International Journal of Pharmaceutics 547 (2018) 244-249.

Zejun Wang et al., Transdermal colorimetric patch for hyperglycemia sensing in diabetic mice, Biomaterials, 237, (2020), 119782.

Yuqi Zhang et al., Advances in Transdermal Insulin Delivery, Adv Drug Deliv Rev., (Jan. 15, 2019), 139: 51-70; doi:10.1016/j.addr.2018.12.006.

Yuanjin Zhao et al., Bio-Inspired Variable Structural Color Materials, Chem. Soc. Rev., (2012), 41, 3297-3317.

Yuanjin Zhao et al., Multifunctional photonic crystal barcodes from microfluidics, NPG Asia Materials (2012) 4, e25; doi:10.1038/am.2012.46.

* cited by examiner

COLLOIDAL CRYSTAL MICRONEEDLE PATCH FOR GLUCOSE MONITORING

RELATED APPLICATION

This Application is a U.S. National Stage filing under 35 U.S.C. § 371 of International Application No PCT/US2022/012973, filed on Jan. 19, 2022, which claims priority to U.S. Provisional Patent Application No. 63/140,206 filed on Jan. 21, 2021, which are hereby incorporated by reference. Priority is claimed pursuant to 35 U.S.C. §§ 119, 371,and any other applicable statute.

STATEMENT REGARDING FEDERALLY SPONSORED RESEARCH AND DEVELOPMENT

This invention was made with government support under Grant Number 1708620, awarded by the National Science Foundation. The government has certain rights in the invention.

TECHNICAL FIELD

The technical field relates a minimally invasive colloidal crystal microneedle patch for naked-eye glucose monitoring. The microneedle patch is able to translate glucose concentrations into naked-eye distinguishable color changes within a few minutes and the responsiveness is reversible.

BACKGROUND

Over 463 million people worldwide are currently diagnosed with diabetes mellitus, a chronic disease characterized by abnormally high blood glucose levels (BGLs). People with type 1 or advanced type 2 diabetes need to self-monitor their BGLs frequently to determine the time and dose of insulin injection. The current electrochemical-based glucometer requires finger-prick blood sampling with consumption of numerous testing strips. This invasive, painful, and costly measurement strategy often needs to be conducted multiple times each day over a life-long time, causing severe physiological and psychological burden to people with diabetes and leading to poor adherence to treatment. Therefore, a minimally invasive, painless, and economical point-of-care testing (POCT) device for BGLs measurement is highly desired.

As a minimally invasive and painless alternative, microneedle (MN) patch devices have been developed and applied for extracting and analyzing interstitial fluid, where many molecular biomarkers are highly correlated with those in the blood. Among studies of leveraging MN patch for glucose monitoring, the colorimetric MN patch system is favorable due to its visualized results without involvement of supporting equipment or complicated procedures. Nonetheless, many of these colorimetric systems contain enzymes and chromogenic substrates, which can induce concerns including enzyme denature, color quenching, by-product toxicity, and non-reusability. Colloidal crystal, a structural color material, offers a promising manner to construct a colorimetric glucose sensor comparing with the enzymatic system. By formulating colloidal crystal with a glucose-responsive material, glucose level could be reported as a structural color of colloidal crystal by manipulating the periodic structure within colloidal crystal through the glucose-responsive material. The colloidal crystal formulated colorimetric glucose sensor is enzyme-free and structural color-based, evading the issues associated with enzymatic formulations. However, the application of colloidal crystal in colorimetric MN patch is still unexplored considering the challenges in formulating sensitive glucose-responsive colloidal crystal (GCC), and assembling soft colloidal crystal with hard microneedles while maintaining the physical properties of colloidal crystal.

SUMMARY

A glucose-responsive colloidal crystal-microneedle (GCC-MN) patch is disclosed for minimally invasive, painless, and naked-eye recognizable glucose colorimetric monitoring as demonstrated in a diabetic mice study. The glucose level may be displayed in situ as a specific color of the patch generated by the glucose-responsive physical nanostructure within the GCC material. To convert physiological glucose levels into naked-eye recognizable structural color signals, the GCC material was formulated by constructing periodic structure inside glucose-responsive fluorophenylboronic acid (FPBA) based matrix with $SiO_2$ nanoparticles (NPs). The GCC material was coated on the surface of a photopolymerized MNs via a secondary photo-crosslinking process mediated by the residual double bonds on the MNs. This core-shell MN structure by assembly of the soft GCC on the exterior of the hard MNs can not only maintain the stimulus-responsive property of the GCC, but also support sufficient mechanical strength of MNs for skin penetration. Upon high glucose levels, increased glucose molecules can bind FPBA within GCC, which increases the hydrophilicity and causes the swelling of $SiO_2$ NPs-embedding GCC. The increased distance between periodically arranged $SiO_2$ NPs results in a redshift of the GCC reflection spectrum, displayed as a color redshift of the GCC-MN patch. Such behavior between glucose and FPBA is glucose concentration-dependent, yielding the GCC-MN patch with the functionality of continuous glucose monitoring. Notably, the optimized GCC formulation exhibited improved glucose responsiveness, manifested as the large spectral shift value (~127 nm) within physiological glucose levels, making home-based POCT feasible. Notably, a separate reader device is not necessarily needed to analyze the color/color changes as these are observable by the user with the naked-eye, although a reader device could be used in some embodiments.

The glucose-responsive colloidal crystal microneedle (GCC-MN) patch was formulated with a core-shell structure with the glucose responsive material contained in the outer shell while the inner core is made from a biocompatible or biosafe resin or polymer material. The GCC-MN patch realized minimally invasive, painless, and naked-eye glucose monitoring in an enzyme-free manner. The GCC material showed improved glucose sensitivity under physiological glucose levels. The GCC material further showed reversible glucose responsiveness thereby making continuous glucose monitoring possible.

In one embodiment, a glucose-responsive colloidal crystal microneedle (GCC-MN) patch is disclosed for monitoring glucose levels in a subject. The patch includes a base having a plurality of microneedles extending away from the surface of the base, wherein the plurality of microneedles include a resin or polymer core surrounded by a shell formed by a glucose-responsive colloidal crystal (GCC) material that includes a glucose-responsive fluorophenylboronic acid (FPBA) based matrix having $SiO_2$ nanoparticles dispersed therein.

The GCC-MN patch is used by applying the GCC-MN patch to the skin of a mammalian subject and ascertaining a color and/or color change of the GCC-MN patch, wherein the color and/or color change is indicative of a level of glucose in the mammalian subject. The color and/or color change may be ascertained by the subject or by another person (e.g., a caregiver, medical provider, or the like). The person that ascertains the color and/or color change may, in some embodiments, use a color chart or the like. In other embodiments, a reader device may be used to ascertain the color or color change of the GCC-MN patch.

The GCC-MN patch is made using a molding operation. First, a mold is provided that has a plurality of surface features defined therein that define the shape of microneedles in the patch (reverse of the microneedles). Next, a first layer of the patch is formed (i.e., the base and inner rigid cores of microneedles) is formed by depositing a resin or polymer over the mold and polymerizing the resin with polymerizing light. The first layer of the patch or the hardened portion containing the microneedle array is then removed from the mold. Next, the glucose-responsive colloidal crystal (GCC) solution (e.g., pre-polymer solution) is added to the mold. The first layer of the patch is then placed onto the mold containing the glucose-responsive colloidal crystal (GCC) solution, wherein a spacer is interposed between the mold and the first layer of the patch. The thickness of the spacer will control the thickness of the shell. The first layer of the patch with the GCC solution is then exposed to polymerizing light to form a shell of GCC material on the microneedles. The now-formed patch is then removed from the mold. The patch can be washed and stored in a buffer solution until use.

In one embodiment, a glucose-responsive colloidal crystal microneedle (GCC-MN) patch for monitoring glucose levels in a subject is disclosed. The GCC-MN patch has a base having a plurality of microneedles extending away from the surface of the base, wherein the plurality of microneedles comprise a resin or polymer core surrounded by a shell comprising glucose-responsive colloidal crystal (GCC) material comprising a glucose-responsive fluorophenylboronic acid (FPBA) based matrix having $SiO_2$ nanoparticles dispersed therein.

In another embodiment, a method of using the GCC-MN patch includes applying the GCC-MN patch to the skin of a mammalian subject and ascertaining a color and/or color change of the GCC-MN patch, wherein the color and/or color change is indicative of a level of glucose in the mammalian subject.

In another embodiment, a method of making glucose-responsive colloidal crystal microneedle (GCC-MN) patch for monitoring glucose levels in a subject includes the operations of: providing a mold having a plurality of surface features defined therein that define the shape of microneedles in the patch; forming a first layer of the patch by depositing a resin or polymer over the mold and polymerizing the resin with polymerizing light; removing the first layer of the patch from the mold; adding a glucose-responsive colloidal crystal (GCC) solution to the mold; placing the first layer of the patch onto the mold containing the glucose-responsive colloidal crystal (GCC) solution, wherein a spacer is interposed between the mold and the first layer of the patch; irradiating the first layer of the patch with polymerizing light to form a shell of GCC material on the microneedles; and removing the formed patch from the mold.

In another embodiment, a kit is provided that includes a glucose-responsive colloidal crystal microneedle (GCC-MN) patch for monitoring glucose levels in a subject having a base having a plurality of microneedles extending away from the surface of the base, wherein the plurality of microneedles comprise a resin or polymer core surrounded by a shell comprising glucose-responsive colloidal crystal (GCC) material comprising a glucose-responsive fluorophenylboronic acid (FPBA) based matrix having $SiO_2$ nanoparticles dispersed therein. The kit includes a color key that is used to correlate a particular color or color change to a specific glucose concentration or range of concentrations. In other embodiments, the kit is provided with or includes a reader device configured to capture images of the GCC-MN patch.

BRIEF DESCRIPTION OF THE DRAWINGS

FIG. 7A shows the surface SEM images of the GCC after treated with i) 100, ii) 200, iii) 300, iv) 400 mg $dL^{-1}$ glucose solutions for 20 min, respectively. FIG. 7B shows the cross-sectional SEM images of the GCC in FIG. 7A. Scale bars: 200 nm.

DETAILED DESCRIPTION OF ILLUSTRATED EMBODIMENTS

Figure 1:
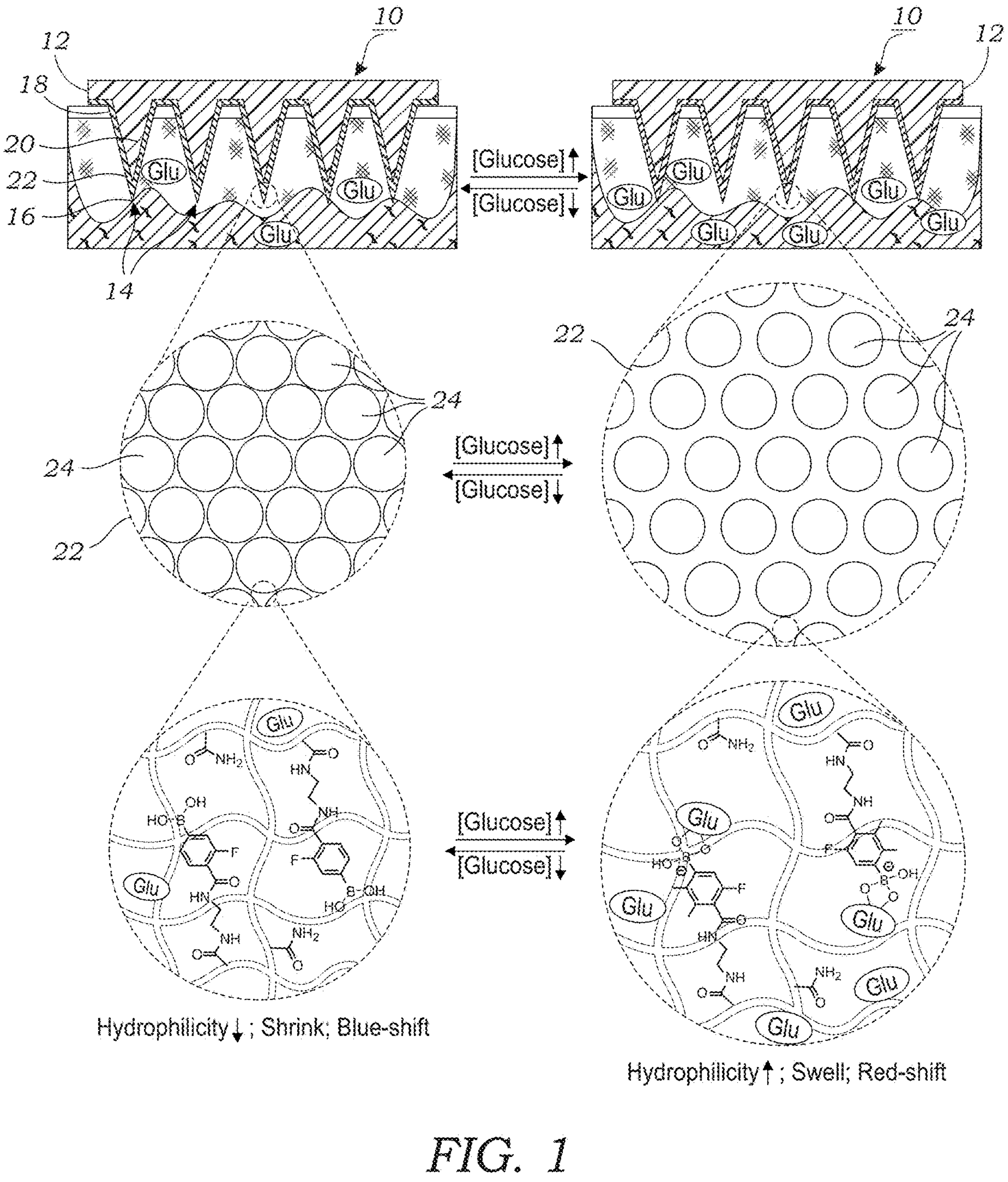
FIG. 1 illustrates a schematic illustration of the MN's glucose-responsive colloidal crystal modified microneedle (GCC-MN) patch, and the mechanism of the GCC-MN patch for naked-eye monitoring of glucose concentrations. At lower glucose concentrations (left), the GCC-MN patch undergoes a blue-shift. At higher glucose concentrations (right), the GCC-MN patch undergoes a red-shift.

FIG. 1 illustrates a glucose-responsive colloidal crystal microneedle (GCC-MN) patch 10 for monitoring glucose levels in a subject (i.e., living mammal). The patch includes a base 12 having a plurality of microneedles 14 extending away from the surface of the base 12. The microneedles 14 generally extend away from the base 12 in an orthogonal direction with respect to the base 12 and may include sharpened tips 16 which aid in penetrating tissue 100 of the subject. The microneedles 14 have a tapered, pyramidal, or conical shape that extends from a base 18 of the microneedles 14 to the tips 16. The height of the microneedles 14 may vary but is typically less than 1 mm in height as measured from the base 18. The width of the base 18 of the microneedles 14 is typically between about 200 vim and about 600 vim. The GCC-MN patch 10 may be placed on any number of tissue 100 types. In one preferred embodiment, the GCC-MN patch 10 is placed on skin tissue 100. The GCC-MN patch 10 may be somewhat flexible to allow the GCC-MN patch 10 to conform to the surface of the applied tissue 100.

With reference to FIG. 1, the plurality of microneedles 14 are formed of a non-biodegradable hardened resin or polymer core 20 that is surrounded on the outside by a shell 22 that is made from a glucose-responsive colloidal crystal (GCC) material. The GCC material that makes up the shell 22 includes a glucose-responsive fluorophenylboronic acid (FPBA) based hydrogel matrix having $SiO_2$ nanoparticles 24 dispersed therein. The shell 22 of the microneedles 14 is softer than the inner core 20. The $SiO_2$ nanoparticles 24 may have diameters within the range of tens of nanometers to hundreds of nanometers.

The core-shell structures of the microneedles 14 is created by the deposting of the soft GCC material that forms the shell 22 on hard microneedle cores 12 that maintains the stimulus-responsive property of the GCC as well as supports sufficient mechanical strength of microneedles 14 for the penetration of tissue 100. The resin or polymer core 20 may be made from a number of biocompatible or biosafe resins or polymers. An example, is clear resin (CLEAR RESIN 1L) obtained from Formlabs Inc., Somerville, USA, CATALOG #RS-F2-GPCL-04. Other polymers may be used including crosslinked polymers formed from, for example, pentaerythritol tetraacrylate (PETA). The resin or polymer should be hard and colorless (i.e., optically transparent). Hardness allows for structural integrity of the patch 10 and enables the microneedles 14 to penetrate the tissue 100. By making the patch 10 substantially optically transparent, color changes and/or color shifts can be readily observed.

With reference to FIG. 1, upon exposure to high glucose levels, increased glucose molecules can bind FPBA within the GCC material of the shell 22, which increases the hydrophilicity and causes the swelling of $SiO_2$ nanoparticles 24 embedded in the GCC material. The increased distance between periodically arranged $SiO_2$ nanoparticles 24 results in a red-shift of the GCC reflection spectrum displayed as a color redshift of the GCC-MN patch 10. Increases in glucose levels results in a red-shift (right side) while a decrease in glucose levels results in a blue-shift (left side) as illustrated in FIG. 1.

Figure 2A:
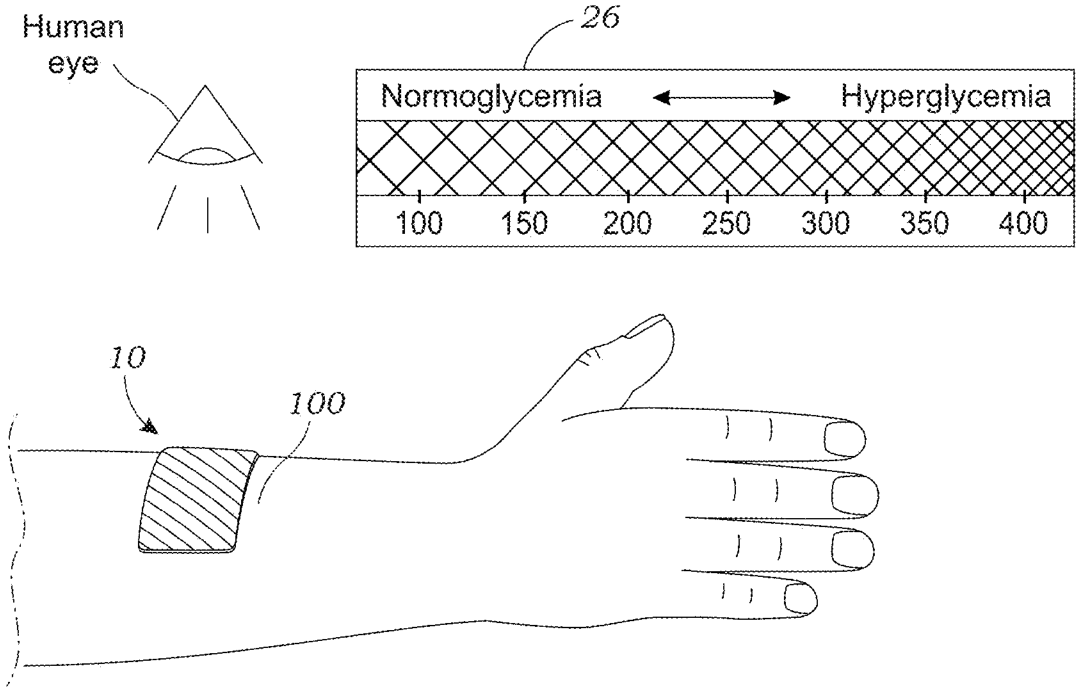
FIG. 2A illustrates a GCC-MN patch applied to the skin of a mammalian subject. The color of the patch is ascertained with the naked eye.
Figure 2B:
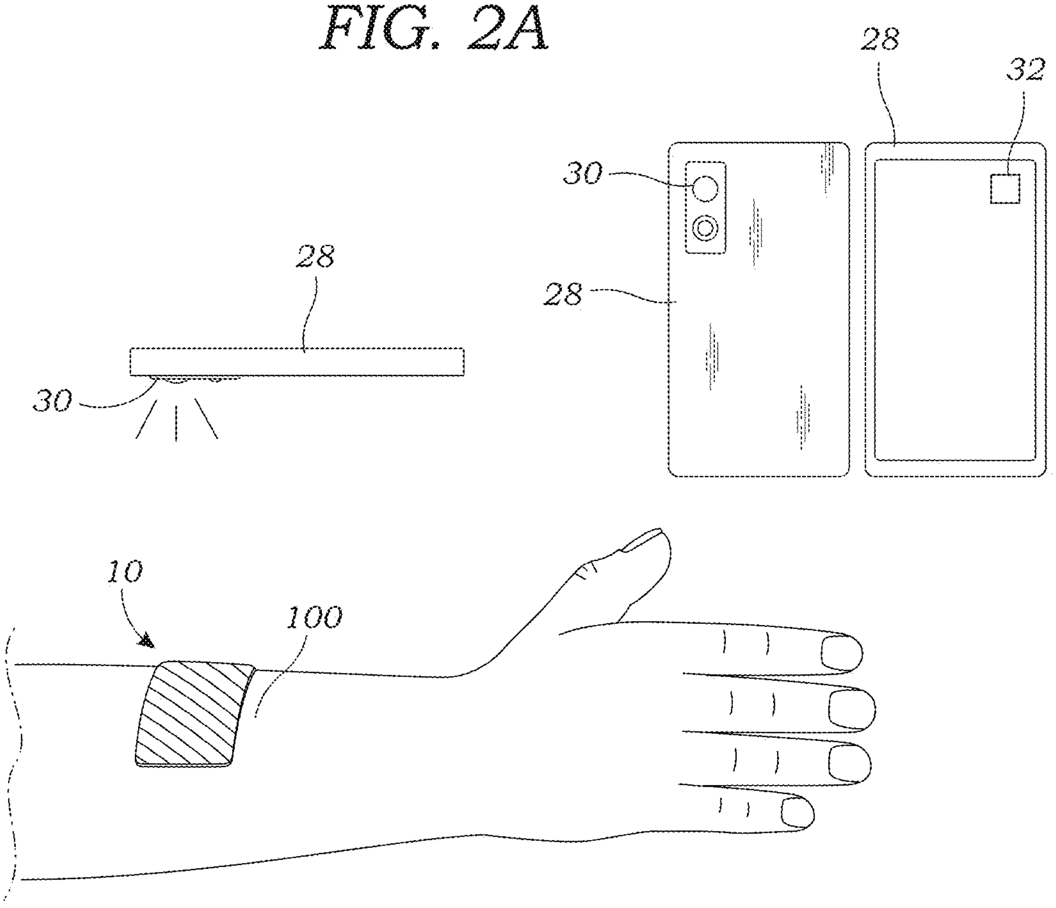
FIG. 2B illustrates a GCC-MN patch applied to the skin of a mammalian subject. The color of the patch is ascertained with a reader device (e.g., mobile phone).

FIG. 2A illustrates one embodiment of how the GCC-MN patch 10 is read. In this embodiment, the subject wearing the GCC-MN patch 10 uses his or her eyes to ascertain the color and/or color change of the patch 10. The color and/or color change of the GCC-MN patch 10 is indicative of a level of glucose in the subject. The subject may be provided with a color key 26 that is used to correlate a particular color or color change to a specific glucose concentration or range of concentrations. This may be a quantitative or qualitative measure of glucose concentrations or concentration range. In one preferred embodiment, the subject is able to ascertain the color and/or color change of the GCC-MN patch 10 with his or her naked-eye. Alternatively, as seen in FIG. 2B, a reader device 28 could be used to ascertain the color and/or color change. For example, the reader device 28 may include a mobile phone with a mobile phone camera 30 that is used to take in image of the patch and software or an application 32 "app" executed thereon may be used to judge the color or other properties (e.g., intensity, hue, etc.) of the GCC-MN patch 10 which can then be used to output or generate a quantitative and/or qualitative measure of glucose as measured by the GCC-MN patch 10. A look-up table or calibration table/graph may be used to map the color properties to the glucose concentration(s) or concentration range(s) output the results which can then be displayed to the user. The color and/or color change of the GCC-MN patch 10 may be ascertained while the GCC-MN patch 10 is disposed on the tissue 100. Alternatively, the color and/or color change of the GCC-MN patch 10 may be ascertained while the GCC-MN patch 10 is removed from the tissue 100.

The binding of glucose to FPBA in the GCC material located on the microneedles 14 is reversible and may operate under repeated cycles thereby allowing for glucose monitoring over an extended period of time (e.g., continuous glucose monitoring). To use the GCC-MN patch 10, the GCC-MN patch 10 is pressed against the skin tissue 100 (or other tissue) so that the microneedles 14 are embedded within the tissue 100. After exposure to the tissue 100, interstitial and other bodily fluids are exposed to and enter the GCC material of the shell 22 and the color and/or color change of the GCC-MN patch 10 can then be ascertained. The GCC-MN patch 10 can be removed by pulling the GCC-MN patch 10 away from the tissue 100 much in the way a conventional bandage is removed from the skin.

To make the patch a series of molding operations are undertaken. First, with reference to FIG. 4A, a mold 50 is provided that has a plurality of surface features defined therein that define the shape of microneedles 14 in the patch 10 (reverse of the microneedles 14). Next, a first layer of the patch is formed (i.e., the base 12 and inner rigid cores 20 of microneedles 14) is formed by depositing a resin or polymer over the mold 50 and polymerizing the resin with polymerizing light (or other polymerizing agent). The first layer of the patch 10 or the hardened portion containing the microneedle core 20 array is then removed from the mold 50. Next, the glucose-responsive colloidal crystal (GCC) solution (e.g., pre-polymer solution) is added to the mold 50. The first layer of the patch 10 is then placed onto the mold 50 containing the glucose-responsive colloidal crystal (GCC) solution, wherein a spacer is interposed between the mold 50 and the first layer of the patch 10. The thickness of the spacer will control the thickness of the shell 22. The thickness of the shell 22 may range from tens of micrometers to several hundreds of micrometers. The first layer of the patch 10 with the GCC solution is then exposed to polymerizing light to form a shell 22 of GCC material on the exterior surface of the microneedles 14. The now-formed GCC-MN patch 10 is then removed from the mold 50. The GCC-MN patch 10 can be washed and stored in a buffer solution until use.

In some embodiments, a kit may be provided to the user that includes one or more of the GCC-MN patches 10 along with the color key 26. The color key 26 may include a card or image that shows a range of colors and the corresponding glucose levels that correspond to each color. Of course, the color key 26 may be provided electronically, for example, as an image that can be downloaded or viewed on a computing device (e.g., mobile phone, tablet, PC and the like). In other embodiments, the kit may include one or more of the GCC-MN patches 10 along with the reader device 28.

EXPERIMENTAL

Materials: $SiO_2$ nanoparticles 24 (140 nm) were purchased from Nanjing Nanorainbow Biotechnology Co., Ltd (Nanjing, China). Acrylamide (≥99%), poly(ethylene glycol) diacrylate (PEGDA, average Mn 700), 2-hydroxy-2-methylpropiophenone (HMPP, 97%), dimethyl sulfoxide (DMSO, ≥99.9%), glucose (≥99.5%) were purchased from Sigma-Aldrich, Inc (St. Louis, USA). 4-((2-Acrylamidoethyl) carbamoyl)-3-fluorophenylboronic acid (FPBA) was synthesized by the method described in A. Matsumoto et al., A synthetic approach toward a self-regulated insulin delivery system, Angew. Chemie Int. Ed. 51 (2012) 2124-2128. doi:10.1002/anie.201106252, which is incorporated herein by reference. Clear resin was purchased from Formlabs Inc (Somerville, USA, CATALOG # is RS-F2-GPCL-04). Sulfo-cyanine5 NHS ester (Cy5) was purchased from Lumiprobe Corp (Maryland, USA). 1,1'-Dioctadecyl-3,3,3',3'-tetramethylindocarbocyanine perchlorate (Dil) was obtained from Invitrogen Corp (California, USA).

Formulation of the GCC (for in vitro characterization only—not patch): FPBA (10.5% w/v), acrylamide (7% w/v), PEGDA (5% w/w of monomers) and HMPP (5% w/w of monomers) were dissolved in 15% v/v $SiO_2$ nanoparticle 24 DMSO suspensions. The resulted GCC precursor solution was infused into the space between two hydrophobic glass slides where a 250 μm spacer was placed, and irradiated with 26.7 mW $cm^{-2}$ 365 nm UV light for 20 min. After that, the photo-polymerized GCC was washed with PBS solution until the residual DMSO in the GCC material was replaced. The obtained GCC was stored in PBS solution for further experiments.

Fabrication of the GCC-MN patch: Clear resin was filled into a microneedle patterned (pyramidal, 400 μm in width, 900 μm in height, 800 μm tip-tip spacing) patch mold 50 under vacuum and was polymerized under UV light (26.7 mW $cm^2$, 365 nm) for 5 min. To increase the mechanical strength, the photo-polymerized first layer of the microneedle patch 10 was further cured under 405 nm light (1.25 mW $cm^{-2}$) for 25 min, and then was detached from the mold 50. The as-prepared GCC precursor solution was infused into the previously used mold 50. Before inserting the cured first layer of the patch 10 into the GCC solution-containing mold, a 250 μm spacer was placed between the first layer of the patch 10 and the mold 50 to control the thickness of the shell 22. Afterward, the GCC precursor solution-containing mold with cured patch 10 was irradiated with 365 nm UV light (26.7 mW cm 2) for 15 min. Finally, the GCC-MN patch 10 was detached from the mold 50, washed, and stored in PBS solution.

In vitro glucose monitoring: To study the glucose responsiveness of the GCC, the GCC or the GCC-MN patch 10 (5×5 array) was immersed in 10 mL glucose-containing PBS solution and observed at different incubation time points.

In vivo glucose monitoring: To evaluate the in vivo glucose responsiveness of the GCC-MN patch 10, diabetic mice (C57BL/6J, Jackson Lab) and normal mice (C57BL/6J, Jackson Lab) were used as the hyperglycemic model and the normoglycemic control, respectively. All animal studies complied with the protocol (ARC #2018-062) approved by the Institutional Animal Care and Use Committee at the University of California, Los Angeles (UCLA). To perform glucose monitoring with the GCC-MN patch 10, the mice were shaved and anesthetized before the experiment. The BGLs of the mice were measured with an Accu-Chek Aviva® meter (Roche Diabetes Care, Inc.) before the GCC-MN patch 10 insertion. Then, the GCC-MN patch 10 was pressed on the skin tissue 100 of the mouse for 10 s and retained for a specific time. Thereafter, the GCC-MN patch 10 was removed from the skin and the color change of the GCC-MN patch 10 was recorded with a camera.

Characterizations: The reflection spectra were recorded with a spectrometer (OCEAN-HDX-XR, Ocean Insight, USA). The SEM images were obtained with a field emission scanning electron microscope (Supra® 40VP, Zeiss, Germany). The 3D fluorescence images were obtained and reconstructed with a confocal microscope (Leica TCS-SP8, Leica Microsystems, Germany) and Imaris software, respectively. The mechanical strength tests were conducted by using the compression mode of Instron 5560 (Instron Corporation, Norwood, Mass.). $^1$H nuclear magnetic resonance spectrum (FIG. 9) was tested with Bruker AV400 broadband FT NMR spectrometer (Bruker, Massachusetts, USA). The averaged hue values were calculated with Adobe Photoshop CC 2017 software.

Results and Discussion

Figure 3A:
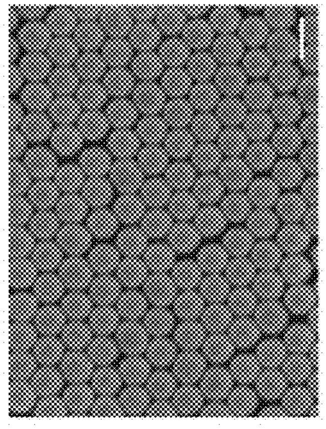
FIG. 3A illustrates the SEM image of $SiO_2$ NPs (140 nm). Scale bar: 200 nm.
Figure 3B:
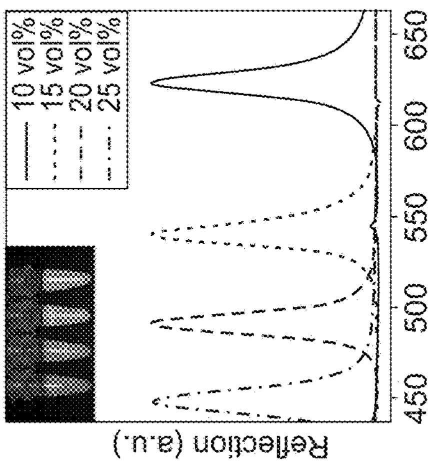
FIG. 3B illustrates the normalized reflection spectra and the digital photograph of $SiO_2$ NPs dispersed solutions.
Figure 3C:
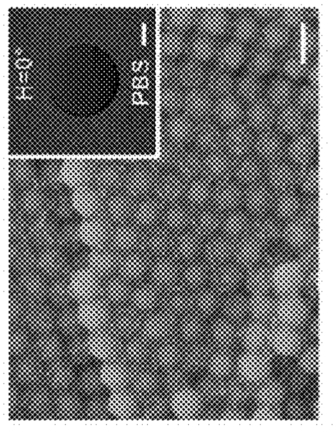
FIG. 3C illustrates an SEM image and optical photo of the GCC. Scale bars: 200 nm and 2 mm.

The structural color of colloidal crystal is dominated by its periodic structure according to Bragg's law:

$$\lambda=1.633dn_{avg} \quad (1)$$

where λ represents the reflection peak wavelength, d is the interplanar distance, and $n_{avg}$ is the averaged refractive index. Thus, the color of colloidal crystal could be manipulated by adjusting the distance d between $SiO_2$ nanoparticles 24 (140 nm diameter, FIG. 3A) through changing the concentration of $SiO_2$ nanoparticles 24 (FIG. 3B). In preparing the GCC, the concentration of $SiO_2$ nanoparticles 24 was set to 15% v/v to ensure the color of the GCC was in the visible region under the physiological glucose concentrations. Glucose-responsive FPBA (10.5% w/v) and acrylamide (7% w/v) were incorporated to construct a glucose-responsive hydrogel network of the GCC. The formulated GCC was colorless since the short distance between the orderly packed $SiO_2$ nanoparticles 24 drove the photonic band gap of the GCC into the invisible UV range (FIG. 3C).

Figure 3D:
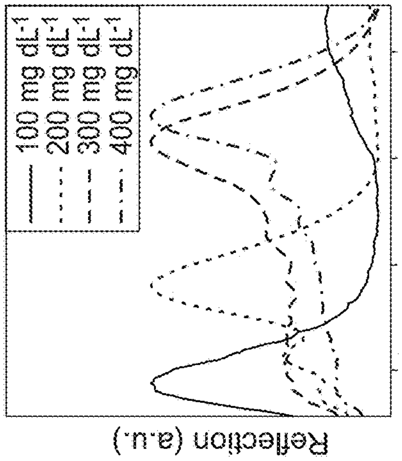
FIG. 3D illustrates the normalized reflection spectra of the GCC after treated with the indicated concentrations of the glucose solutions for 20 min.
Figure 6:
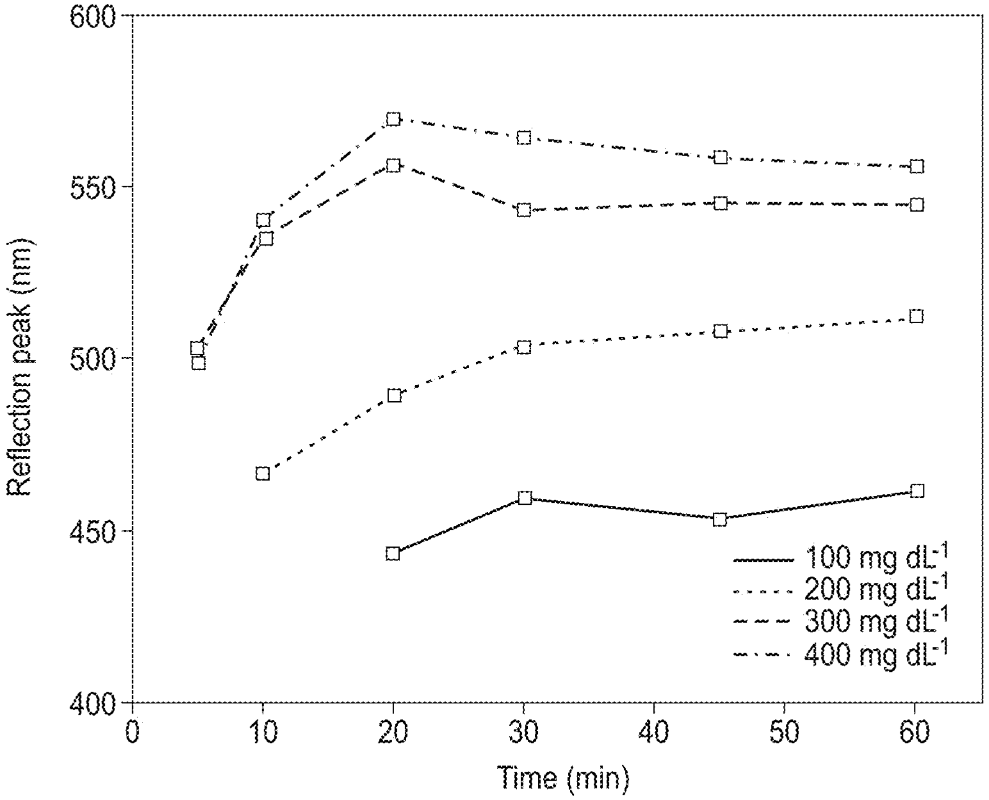
FIG. 6 illustrates the reflection peak positions of the GCC in different glucose solutions (100, 200, 300, and 400 mg $dL^{-1}$) for a different immersion duration. The data are presented as mean±SD (n=3).

The color and the structure of the GCC changed while immersed into various concentrations of glucose solutions (100, 200, 300, and 400 mg $dL^{-1}$). The reflection peak of the GCC red-shifted with the prolonged reaction time and increased glucose concentration (FIG. 6). Here, the reaction time was set to 20 min for the following characterizations to achieve distinct color discrimination of the GCC under different glucose concentrations. The reflection peak of the GCC shifted from 443 nm to 570 nm (127 nm spectral shift) when the glucose concentration was increased from 100 to 400 mg $dL^{-1}$ (FIG. 3D), demonstrating the excellent glucose responsiveness and the feasibility of the GCC as a naked-eye recognizable colorimetric glucose sensor. The GCC exhibited specific colors under different glucose concentrations, specifically the color of the GCC changed from violet (100 mg $dL^{-1}$ glucose) to blue (200 mg $dL^{-1}$ glucose), and further to green (400 mg $dL^{-1}$ glucose) by increasing glucose concentration (FIG. 3E).

Figure 3E:
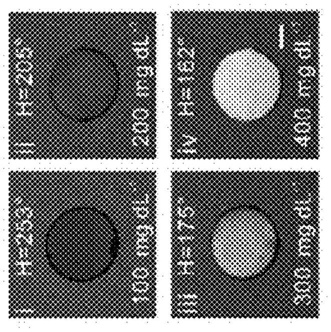
FIG. 3E illustrates the corresponding digital images of the GCC in FIG. 3D. Scale bar: 2 mm. H represents the averaged hue value of the GCC.
Figure 3F:
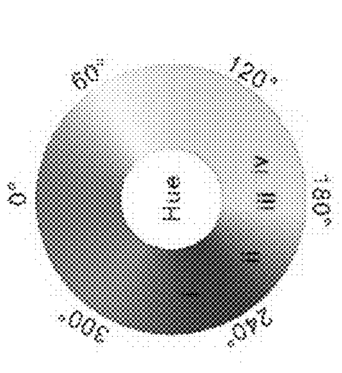
FIG. 3F is an image of a hue circle where the images in FIG. 3E are marked at the corresponding positions.
Figure 3G:
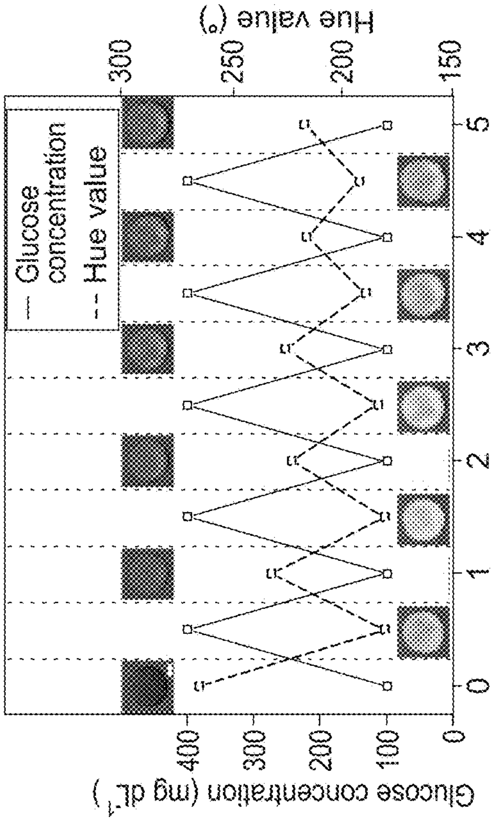
FIG. 3G illustrates the reversibility of the GCC after treated with different glucose solutions. The GCC was immersed in 100 and 400 mg $dL^{-1}$ glucose solutions for 20 min alternately. After 5 cycles the color and the averaged hue value of the GCC were still reversible. Scale bar: 2 mm.
Figure 7A:
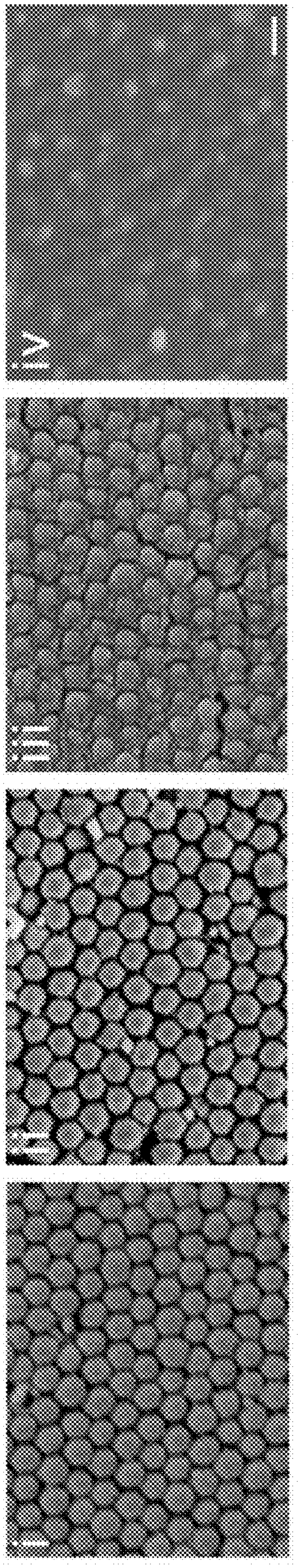
FIGS. 7A and 7B illustrates the SEM images of the GCC under different glucose concentrations.
Figure 7B:
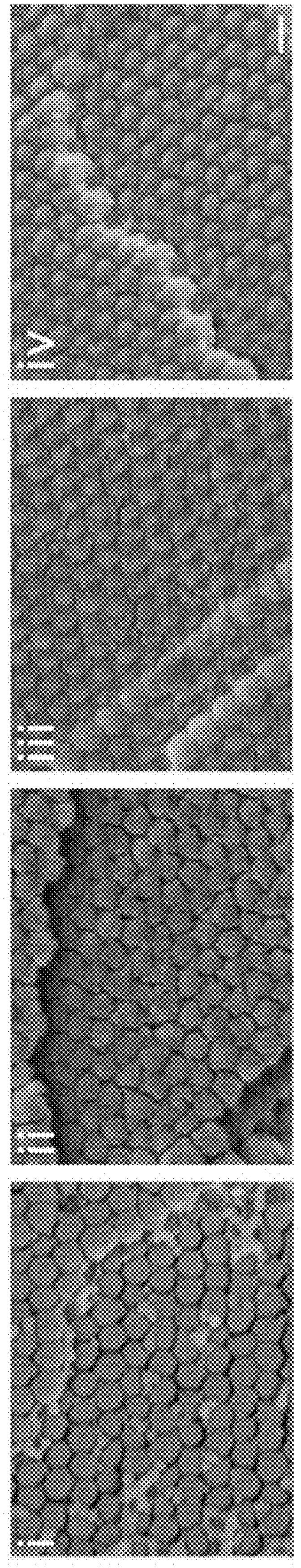
Figure 8:
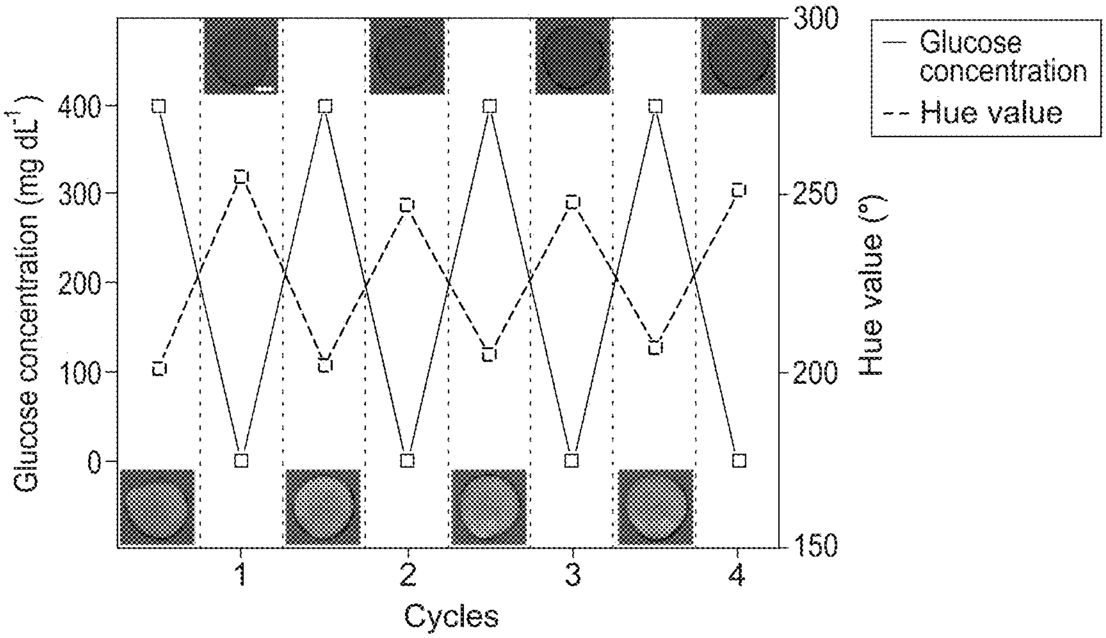
FIG. 8 illustrates the recyclability of the GCC. After washed with PBS solution, the glucose treated GCC could return to colorless and be reused for glucose detection. Scale bar: 2 mm.

To quantify the color of the GCC, averaged hue value (H), the color appearance parameter, of the GCC under different glucose concentrations was measured and presented in a hue circle (FIGS. 3E and 3F). The averaged hue values of the GCC decreased with increased glucose concentrations, owing to the redshift of GCC color in response to elevated glucose concentrations. Upon high glucose concentrations, increased glucose molecules bind to FPBA, enhancing the hydrophilicity of the GCC and causing the GCC to swell. This is supported by the SEM images, which depicted the enlarged particle distance and expanded hydrogel network (FIGS. 7A, 7B). The binding of glucose to FPBA is reversible, thus the FPBA-based formulation shows reversible glucose responsiveness. The GCC was put in 100 mg $dL^{-1}$ and 400 mg $dL^{-1}$ glucose solutions alternately, during which the color and averaged hue value of the GCC displayed reversible changes even after five (5) cycles (FIG. 3G). The reversible glucose responsiveness endows the GCC with the ability to be used for continuous glucose monitoring and recyclability (FIG. 8).

Figure 4A:
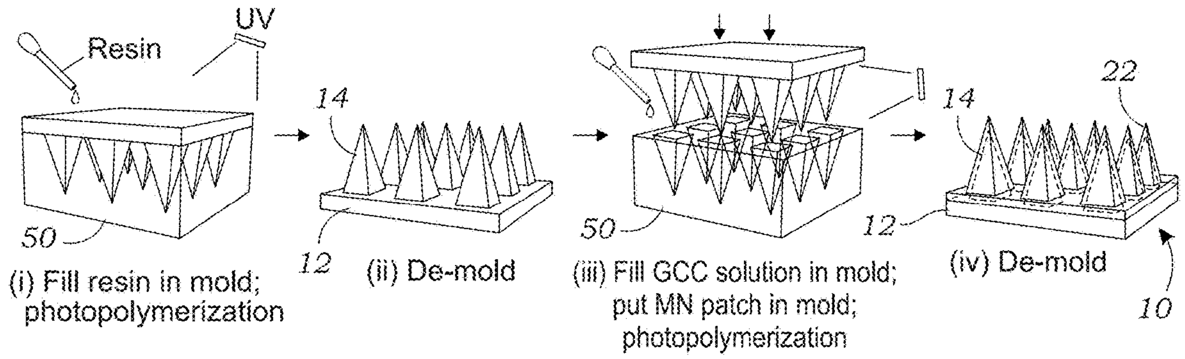
FIG. 4A schematically illustrates the fabrication process of the GCC-MN patch. The insets are the photographs of bare MN patch and the GCC-MN patch, respectively. Scale bars: 1 mm.
Figure 4B:
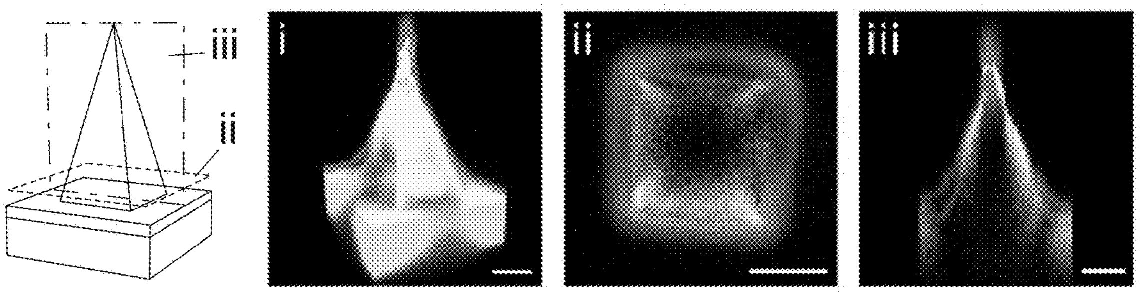
FIG. 4B shows confocal microscopy images of the GCC-MN. Image (i) shows the three-dimensional reconstructed confocal image. Images (ii-iii) show the cross-sectional confocal images taken along orthogonal planes (i) and (ii). Scale bars: 200 μm.
Figure 4C:
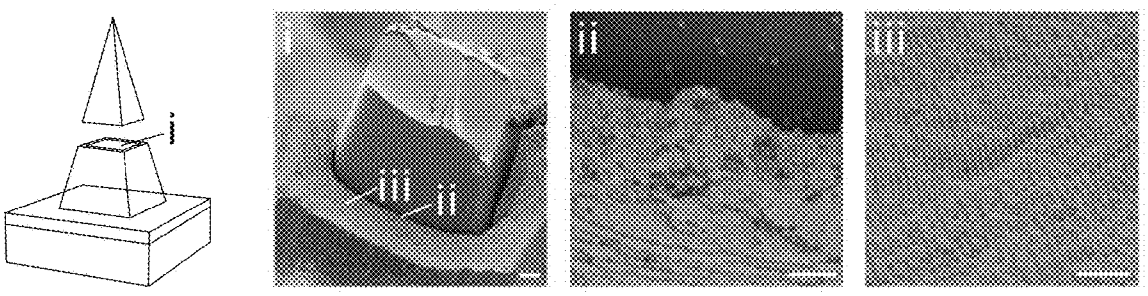
FIG. 4C shows SEM images of the GCC-MN structure. Image (i) shows the cross-sectional SEM image of the GCC-MN. Images (ii-iii) show the magnified views of (i). Scale bars: 1 μm.
Figure 9:
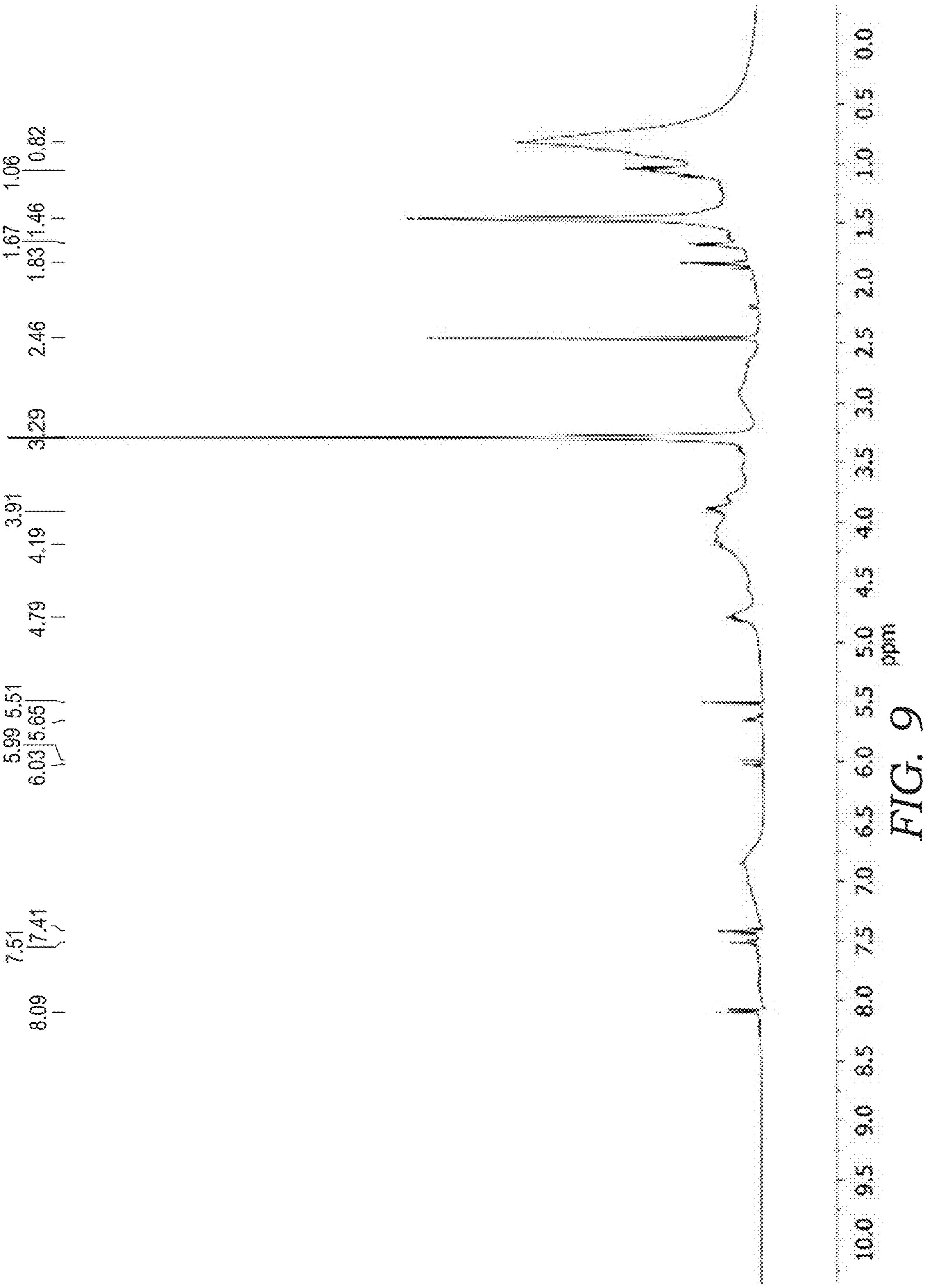
FIG. 9 shows the $^1$H-NMR spectrum of clear resin in DMSO-$d_6$.

To assemble the soft GCC together with the hard microneedles 14 while maintaining both of the glucose responsiveness of the GCC and the ability of microneedles 14 to puncture the skin tissue 100, the GCC was secondarily modified on the surface of microneedles 14 through photo-crosslinking. As illustrated in FIG. 4A, the resin was infused into a microneedle shape-containing mold 50 and photo-crosslinked by UV light. The cured first layer of the patch 10 was then put into the mold 50 containing GCC precursor solution and photo-crosslinked by UV light for the second time. In that way, the GCC was coated on the surface of the microneedles 14 by cross-linking with the residual double bonds on the microneedles 14 (FIG. 9). Confocal microscopy and scanning electron microscopy (SEM) were leveraged to evaluate the morphology of the GCC-MN patch 10. As shown in the three-dimensional reconstructed confocal images, distinguished boundary and close contact between Cy5-labeled GCC and Dil-labeled MN were identified (FIG. 4B), confirming the GCC was coated on the microneedle 14. Furthermore, the periodic structure within the GCC, which is the guarantee of the colorimetric feasibility of the GCC-MN patch 10, was investigated. The GCC-coated microneedle 14 was cut off from the middle and the cross-section was observed with SEM. The residual hydrogel network was firmly attached to the exterior of the microneedle 14, and the $SiO_2$ nanoparticles 24 within GCC shell 22 were orderly packed in the hydrogel networks, which was similar to that of the GCC (FIG. 4C).

Figure 4D:
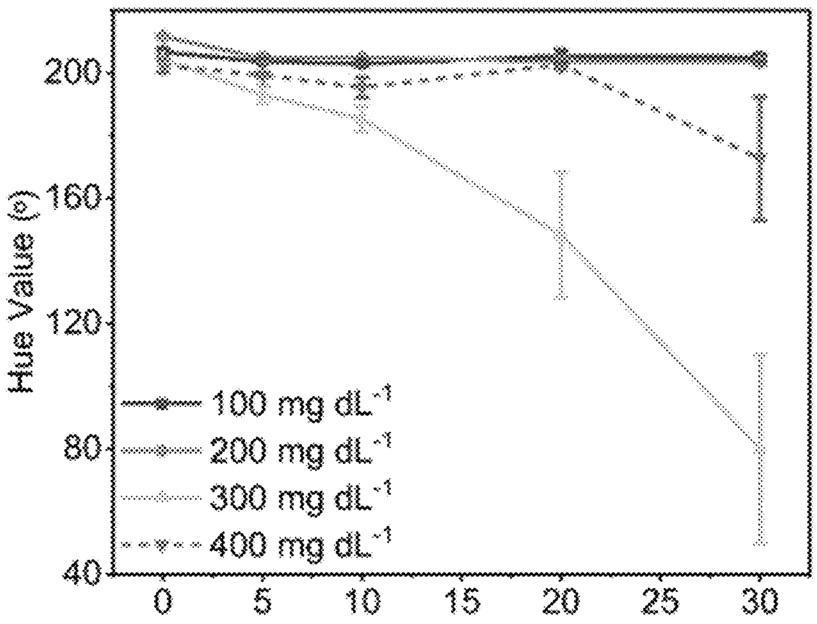
FIG. 4D is a graph showing the averaged hue value of the GCC-MN after treated with different glucose solutions (100, 200, 300, and 400 mg $dL^{-1}$) for different times. The data are presented as mean±SD (n=3).
Figure 4E:
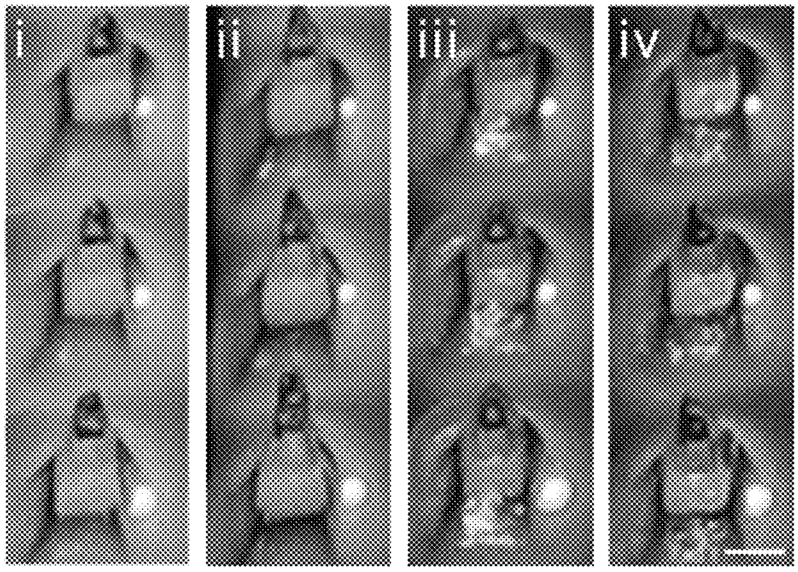
FIG. 4E are digital images of the GCC-MN treated with i) 100, ii) 200, iii) 300, iv) 400 mg $dL^{-1}$ glucose solutions for 30 min, respectively. Scale bar: 200 μm.
Figure 10:
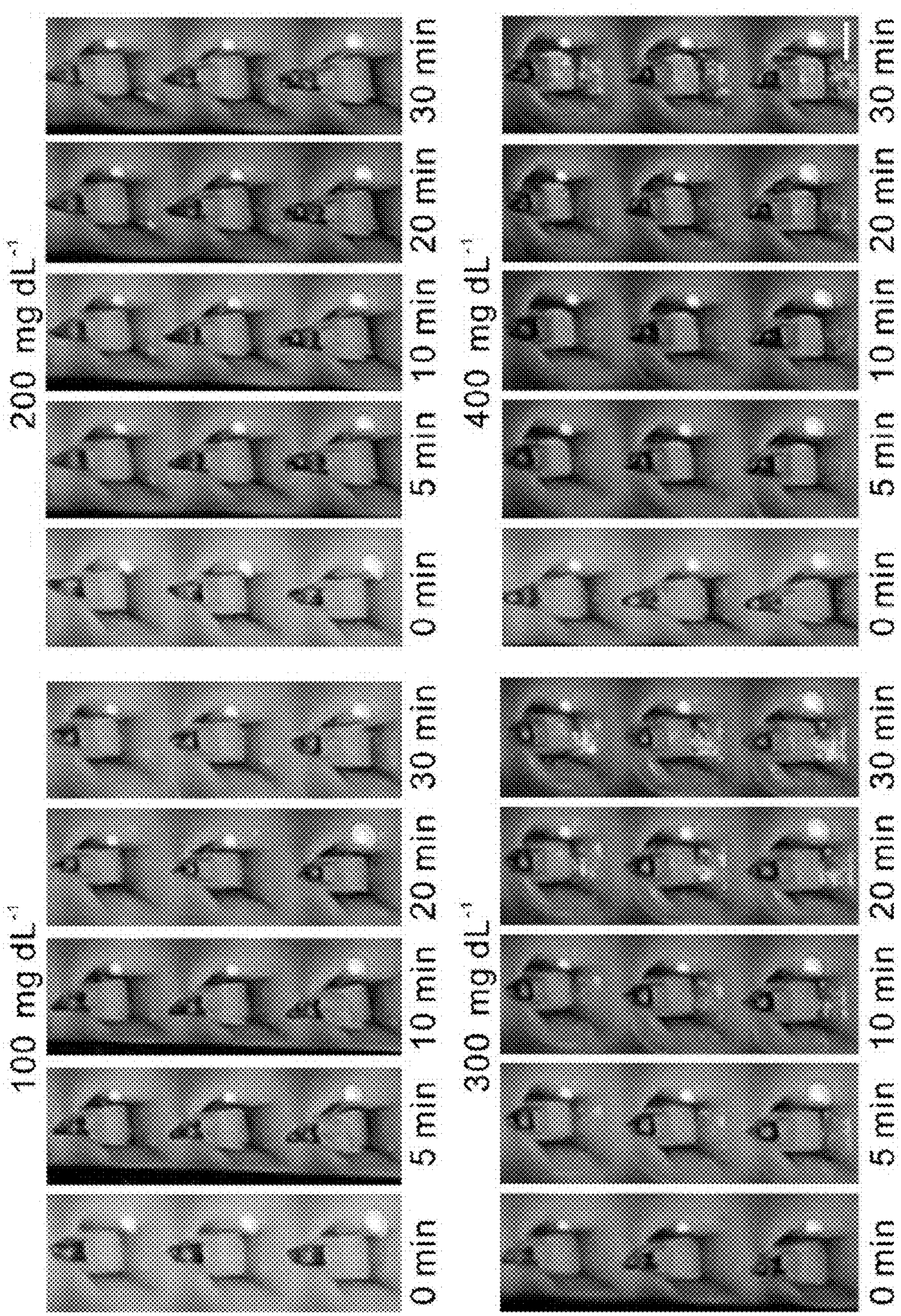
FIG. 10 illustrates the in vitro study of glucose responsiveness of the GCC-MN. The GCC-MN was immersed in different glucose solutions respectively, and the images were recorded at different time points. Scale bar: 200 μm.

The in vitro glucose responsiveness of the GCC-MN patch 10 was evaluated by exposing the core-shell MN patches 10 into different glucose solutions (100, 200, 300, and 400 mg $dL^{-1}$) for various periods (0, 5, 10, 20, and 30 min). Their averaged hue values were subsequently calculated (FIG. 10 and FIG. 4D). The hue value of the GCC-MN patch 10 did not change significantly when the glucose concentration was below 200 mg $dL^{-1}$. When the glucose concentration was increased to 300 mg $dL^{-1}$, an obvious green color accompanied by a dramatic drop in hue value was identified within 5 min (FIG. 10). As the immersion time increased, the color of the GCC-MN patch 10 further redshifted to yellow and the hue value dropped over a period of 30 min. A similar redshift was also observed for the GCC-MN patch 10 when it was exposed to a 400 mg $dL^{-1}$ glucose solution where the color of the GCC-MN patch 10 redshifted to red in 30 min. It is worth mentioning that the averaged hue value of the GCC-MN patch 10 under 400 mg $dL^{-1}$ glucose concentration (dashed line in FIG. 4D) did not drop as expected. This is due to the interference caused by the hue value of red (0° or 360°) to the averaged hue value calculation. The color redshift trend of the GCC-MN patch 10 in response to the elevated glucose concentrations (FIG. 4E) was similar to that of the GCC alone. The slight color difference between the GCC-MN patch 10 and the GCC alone under a specific glucose concentration might be attributed to the experimental variables caused by the different fabrication processes. Collectively, the formulated GCC-MN patch 10 could change color in a glucose-responsive manner, especially when the glucose concentration was over 200 mg $dL^{-1}$, the condition that mouse is considered to be hyperglycemia.

Figure 5A:
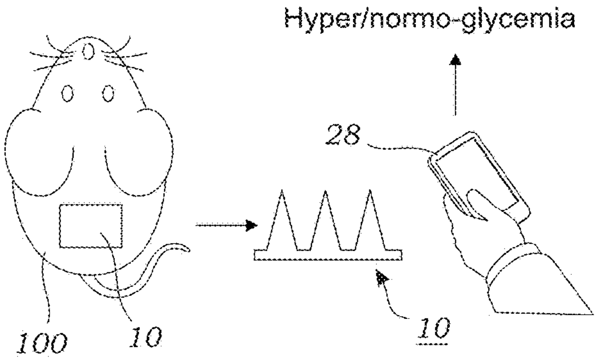
FIG. 5A is a schematic representation of in vivo monitoring glucose levels with the GCC-MN patch in a mouse model. The hyperglycemia or normoglycemia could be identified with eyes or camera according to the color change of the GCC-MN patch.
Figure 5B:
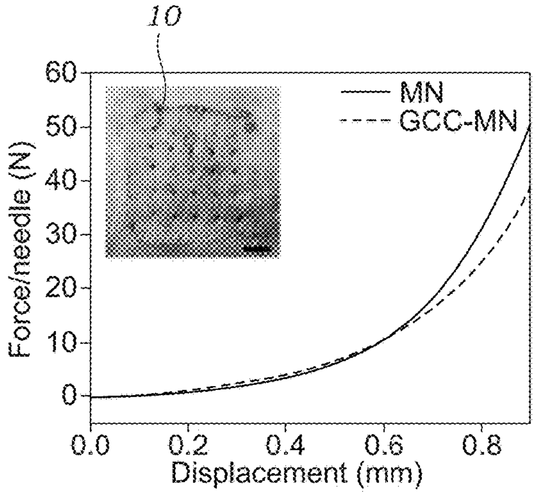
FIG. 5B is a graph showing the mechanical characterizations of the GCC-MN and bare microneedle (without GCC). The inset is the trypan blue stained mouse skin after applied with the GCC-MN patch. Scale bar: 1 mm.
Figure 5C:
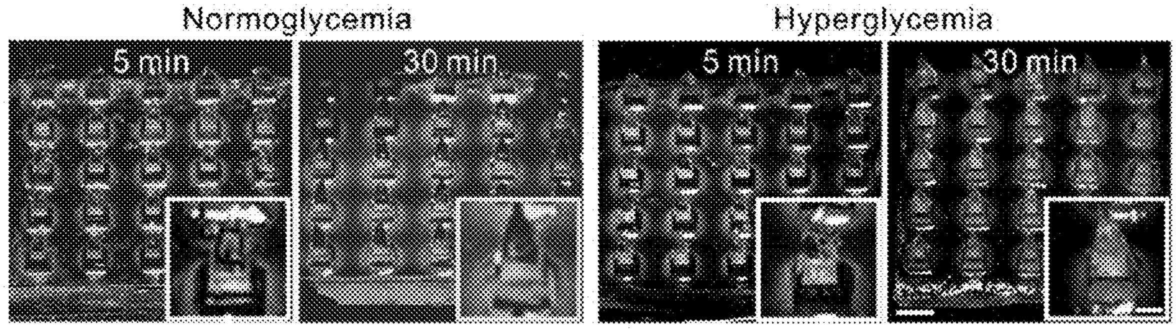
FIG. 5C are digital images of the GCC-MN patches after inserting normoglycemic (~180 mg $dL^{-1}$ glucose) or hyperglycemic (~400 mg $dL^{-1}$ glucose) mice skins for a different time. Scale bars: 500 μm, 200 μm (the inset).
Figure 5D:
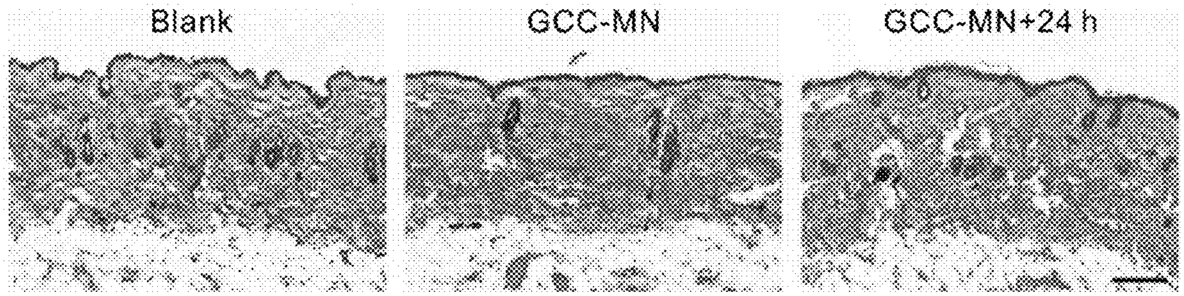
FIG. 5D are H&E staining images of untreated mouse skin, mouse skin after applied with GCC-MN patch, and mouse skin one day after GCC-MN patch treatment, respectively. The GCC-MN patch treatment time is 30 min. Scale bar: 100 μm.

The secondary modification design integrated the gel-like GCC with the skin-penetrating MN scaffold, allowing the minimally invasive in vivo study (FIG. 5A) with soft materials. The GCC-MN patch 10 showed a similar mechanical property with unmodified microneedles, and no fracture (force) was observed during the test, demonstrating that the hardness and toughness of the microneedles 14 were well maintained after the GCC coating (FIG. 5B). The GCC-MN patch 10 was further inserted into the mouse skin tissue 100 which was subsequently stained by trypan blue, confirming the insertion capability of the GCC-MN (FIG. 5B). The in vivo glucose monitoring study with the GCC-MN patch 10 was performed on both streptozotocin (STZ)-induced C57BL/6J diabetic mice and healthy C57BL/6J mice, which served as the hyperglycemic model and the normoglycemic control, respectively. Five min after the GCC-MN patch 10 application, the patches 10 were removed and analyzed. The GCC-MN patches 10 remained colorless in the control group, while the GCC-MN patches 10 used in the hyperglycemic group displayed a green color (FIG. 5C). Considering the interaction between the GCC-MN patch 10 and interstitial fluid is time-dependent, the application time of the GCC-MN patch 10 on the mouse was further prolonged to 30 min. A significantly distinguished color change was observed for the GCC-MN patch 10 in the hyperglycemic group, while the GCC-MN patch 10 applied to the normal mouse remained colorless (FIG. 5C), demonstrating the feasibility of GCC-MN patch 10 for hyperglycemia monitoring in the diabetic mouse. Of note, the GCC-MN patch 10 is enzyme-free and dye-free, eliminating the associated biocompatibility issues. Hematoxylin and eosin (H&E) staining of the mouse skins obtained from the treated sites of the GCC-MN patch 10 was performed. The skin showed negligible inflammation after GCC-MN patch 10 insertion as compared to the untreated skin, proving biosafety of the GCC-MN patch 10 (FIG. 5D).

A GCC-MN patch 10 was developed for minimally invasive, painless, and naked-eye recognizable glucose colorimetric monitoring. The GCC showed improved glucose sensitivity, rendering naked-eye glucose monitoring feasible. The secondary modification strategy integrated the GCC with MN, which enabled the in vivo glucose colorimetric monitoring with naked eyes in an enzyme-free way. As demonstrated in a diabetic mouse model, the GCC-MN patch 10 was qualified to in situ detect hyperglycemia in mice without significant inflammation concern. With this secondary modification method, the microneedle-containing patch could be tailored with theranostic functions (with the GCC material in this specific implementation) for broad applications beyond glucose monitoring in drug delivery and POCT fields.

While embodiments of the present invention have been shown and described, various modifications may be made without departing from the scope of the present invention. For example, in some embodiments, the GCC-MN patch 10 may include an adhesive which aids in keeping the GCC-MN patch 10 secured to the tissue 100. A fastener (e.g., band) or backing material may also be provided on the GCC-MN patch 10 to aid in securing the GCC-MN patch 10 to the tissue 100. The invention, therefore, should not be limited, except to the following claims, and their equivalents.

What is claimed is:

1. A glucose-responsive colloidal crystal microneedle (GCC-MN) patch for monitoring glucose levels in a subject comprising:
- a base having a plurality of microneedles extending away from the surface of the base, wherein the plurality of microneedles comprise a resin or polymer core surrounded by a shell comprising glucose-responsive colloidal crystal (GCC) material comprising a glucose-responsive fluorophenylboronic acid (FPBA) based matrix having $SiO_2$ nanoparticles dispersed therein.

2. The GCC-MN patch of claim 1, wherein the height of the plurality of microneedles is less than about 1 mm.

3. The GCC-MN patch of claim 1, wherein the width of the plurality of microneedles is between about 200 μm and 600 μm at the base.

4. The GCC-MN patch of claim 1, wherein the resin or polymer is non-biodegradable.

5. The GCC-MN patch of claim 1, wherein the glucose-responsive FPBA based matrix comprises a hydrogel.

6. The GCC-MN patch of claim 5, wherein the glucose-responsive FPBA based matrix is formed from a mixture of 4-((2-Acrylamidoethyl) carbamoyl)-3-fluorophenylboronic acid (FPBA), acrylamide, poly(ethylene glycol) diacrylate (PEGDA), and 2-hydroxy-2-methylpropiophenone (HMPP).

7. The GCC-MN patch of claim 1, wherein the patch is substantially optically transparent.

8. A method of using the GCC-MN patch of claim 1 comprising:
- applying the GCC-MN patch to the skin of a mammalian subject; and
- ascertaining a color and/or color change of the GCC-MN patch, wherein the color and/or color change is indicative of a level of glucose in the mammalian subject.

9. The method of claim 8, wherein color comprises a hue representation.

10. The method of claim 8, wherein the color and/or color change of the GCC-MN patch is ascertained with the naked-eye.

11. The method of claim 8, wherein the color and/or color change of the GCC-MN patch is ascertained with a reader device.

12. The method of claim 8, wherein the color and/or color change is ascertained while the GCC-MN patch is disposed on the skin.

13. The method of claim 8, wherein the color and/or color change is ascertained after the GCC-MN patch is removed from the skin.

14. A method of making glucose-responsive colloidal crystal microneedle (GCC-MN) patch for monitoring glucose levels in a subject comprising:
- providing a mold having a plurality of surface features defined therein that define the shape of microneedles in the patch;
- forming a first layer of the patch by depositing a resin or polymer over the mold and polymerizing the resin with polymerizing light;
- removing the first layer of the patch from the mold;
- adding a glucose-responsive colloidal crystal (GCC) solution to the mold;
- placing the first layer of the patch onto the mold containing the glucose-responsive colloidal crystal (GCC) solution, wherein a spacer is interposed between the mold and the first layer of the patch;
- irradiating the first layer of the patch with polymerizing light to form a shell of GCC material on the microneedles; and
- removing the formed patch from the mold.

15. The method of claim 14, further comprising washing the formed patch and storing the patch in a buffered solution.

16. The method of claim 14, wherein the GCC solution comprises a mixture of 4-((2-Acrylamidoethyl) carbamoyl)-3-fluorophenylboronic acid (FPBA), acrylamide, poly(ethylene glycol) diacrylate (PEGDA), and 2-hydroxy-2-methylpropiophenone (HMPP), and $SiO_2$ nanoparticles.

17. The method of claim 14, wherein the operation of forming a first layer of the patch comprises depositing a resin or polymer over the mold and polymerizing the resin multiple cycles of polymerizing light.

18. A kit comprising:
- a glucose-responsive colloidal crystal microneedle (GCC-MN) patch for monitoring glucose levels in a subject having a base having a plurality of microneedles extending away from the surface of the base, wherein the plurality of microneedles comprise a resin or polymer core surrounded by a shell comprising glucose-responsive colloidal crystal (GCC) material comprising a glucose-responsive fluorophenylboronic acid (FPBA) based matrix having $SiO_2$ nanoparticles dispersed therein; and a color key that is used to correlate a particular color or color change to a specific glucose concentration or range of concentrations; or a reader device configured to capture images of the GCC-MN patch.

* * * * *